US008580316B2

(12) United States Patent
Boehm et al.

(10) Patent No.: US 8,580,316 B2
(45) Date of Patent: Nov. 12, 2013

(54) IMMUNE STIMULATORY INFANT NUTRITION

(75) Inventors: Günther Boehm, Echzell (DE); Christopher Beermann, Neu-Anspach (DE); Bernd Stahl, Rosbach (DE); Laura M'Rabet, Amersfoort (NL); Johan Garssen, Nieuwegein (NL)

(73) Assignee: N. V. Nutricia, Zoetermeer (NL)

( * ) Notice: Subject to any disclaimer, the term of this patent is extended or adjusted under 35 U.S.C. 154(b) by 0 days.

(21) Appl. No.: 13/360,508

(22) Filed: Jan. 27, 2012

(65) Prior Publication Data

US 2012/0195975 A1    Aug. 2, 2012

Related U.S. Application Data

(63) Continuation of application No. 11/660,594, filed as application No. PCT/EP2005/008999 on Aug. 19, 2005, now Pat. No. 8,114,441.

(30) Foreign Application Priority Data

Aug. 20, 2004  (EP) ..................... 04019856

(51) Int. Cl.
*A61K 38/16*  (2006.01)
*A61K 33/30*  (2006.01)
*A61P 17/00*  (2006.01)
*A61P 37/08*  (2006.01)
*A61P 29/00*  (2006.01)
*A61P 1/12*  (2006.01)

(52) U.S. Cl.
USPC .............. 424/643; 514/5.6; 514/557; 514/23; 514/53; 514/2; 426/583; 426/64; 426/74; 426/658

(58) Field of Classification Search
USPC ................... 424/643; 514/5.6, 557, 23, 53, 2; 426/583, 64, 74, 658
See application file for complete search history.

(56) References Cited

U.S. PATENT DOCUMENTS

| 5,374,657 A | 12/1994 | Kyle |
| 5,472,952 A | 12/1995 | Smidt et al. |
| 5,792,501 A | 8/1998 | Lepine |
| 5,792,754 A | 8/1998 | Green et al. |
| 6,245,379 B1 | 6/2001 | Lepine |
| 6,376,544 B2 | 4/2002 | Lowry et al. |
| 6,777,391 B1 | 8/2004 | Kratky et al. |
| 2004/0143013 A1 | 7/2004 | Schade et al. |

FOREIGN PATENT DOCUMENTS

| CA | 2340103 | 2/2000 |
| EP | 0 756 828 B1 | 11/1998 |
| EP | 1 242 436 B1 | 11/2004 |
| WO | WO-95/17102 A | 6/1995 |
| WO | WO-98/46764 A1 | 10/1998 |
| WO | WO-02/42484 A2 | 5/2002 |
| WO | WO-03/102205 A1 | 12/2003 |
| WO | WO-2004/002495 A1 | 1/2004 |
| WO | WO-2005/039597 A2 | 5/2005 |

OTHER PUBLICATIONS

Ganglioside: retrieved from internet: http://en.wikipedia.org/wiki/Sialic_acid. Retrieved on Jan. 28, 2013.*
Alles et al., "Current trends in the composition of infant milk formulas," Current Paediatrics, vol. 14, 2004, pp. 51-63.
Carlson, "N-Acetylneuraminic acid concentrations in human milk oligosaccharides and glycoproteins during lactation," American Journal of Clinical Nutrition, vol. 41, Apr. 1985, pp. 720-726.
Consolidation Text produced by CONSLEG system of the Office for Official Publications of the European Communities, Commission Directive on infant formulae and follow-on formulae, (CONSLEG: 1991L0321—Jan. 5, 2004), 27 pages.
Deizenne et al., "Effect of Fermentable Fructo-Oligosaccharides on Mineral, Nitrogen and Energy Digestive Balance in the Rat," Life Sciences, vol. 57, No. 17, 1995, pp. 1579-1587.
Gurr, "Review of the progress of Dairy Science: Human and artificial milks for infant feeding," Journal of Dairy Research, vol. 48, 1981, pp. 519-554.
International Search Report for PCT/EP2005/008999 dated Mar. 21, 2006, 3 pages.
Jenness et al., "Principles of Dairy Chemistry." John Wiley & Sons, Inc., NY, 2010, pp. 114, 115, 120, 121, 124, 125 and 154-157.
Neeser et al., "Quantitative Determination of Complex Carbohydrates in Bovine Milk in Milk-Based infant Formulas," Journal of Dairy Science, vol. 74, No. 9, 1991, pp. 2660-2871.
"Opinion of the Science Panel on Dietetic Products, Nutrition and Allergies on a request from the Commission relating to the safety and suitability for particular nutritional use by infants of fructooligosaccharides in infant formulae and follow-on formulae," The EFS Journal, vol. 31, 2004, pp. 1-11.
"Paper for information Fructo-oligosaccharides (FOS) and Galacto-oligosaccharides (GOS) in infant Formulae," Scientific Advisory Committee on Nutrition, SACN/02/01, Agenda Item 7, Mar. 27, 2001, 1 page.
Reeves et al., "AIN-93 Purified Diets for Laboratory Rodents: Final Report of the American Institute of Nutrition Ad Hoc Writing Committee on the Reformulation of the AIN-76A Rodent Diet," J. Nutr., vol. 123, 1993, pp. 1939-1951.

(Continued)

Primary Examiner — Ernst Arnold
Assistant Examiner — Hong Yu
(74) Attorney, Agent, or Firm — Gilberto M. Villacorta; Sunit Talapatra; Foley & Lardner LLP

(57) ABSTRACT

A nutritional or pharmaceutical composition comprising fat, protein, carbohydrate, whey and casein is provided. The composition has a weight ratio of casein to whey between 1:1 to 1:2.4 and comprises: a) at least 3 grams arginine per 100 grams protein; b) at least 10 wt. % linoleic acid based on total fatty acids; c) at least 1 wt. % alpha linolenic acid based on total fatty acids; d) at least one long chain-polyunsaturated fatty acid in an amount exceeding 0.1 wt. % based on total fatty acids selected from docosahexaenoic acid, arachidonic acid and eicosapentaenoic acid; e) 5 to 25 wt. % of at least one polyunsaturated fatty acid based on total fatty acids; and 2 to 12 grams indigestible oligosaccharides having a degree of polymerisation of 2 to 100 per 100 gram dry weight of the composition. Methods of treatment by administering the composition are also provided.

14 Claims, No Drawings

(56) References Cited

OTHER PUBLICATIONS

Wang et al., "Concentration and distribution of sialic acid in human milk and infant formulas," American Society for Clinical Nutrition, vol. 74, 2001, pp. 510-515.

Wang et al., "The role and potential of sialic acid in human nutrition," European Journal of Clinical Nutrition, vol. 57, 2003, pp. 1351-1369.

Yoshida et al., "Alginic Acid Oligosaccharide Suppresses Th2 Development and IgE production by Inducing IL-12 Production," Int'l. Archives of Allergy and Immunology, 2004.

* cited by examiner

IMMUNE STIMULATORY INFANT NUTRITION

CROSS-REFERENCE TO RELATED PATENT APPLICATIONS

This application is a Continuation of U.S. patent application Ser. No. 11/660,594, filed Aug. 9, 2007, which is a National Stage of PCT/EP2005/008999, filed Aug. 19, 2005, which also claims priority to EP 04019856.6, filed Aug. 20, 2004, all of which are incorporated herein by reference in their entirety.

FIELD OF THE INVENTION

The present invention relates to a nutritional or pharmaceutical composition containing a fat component, a protein component and a carbohydrate component and comprising whey and casein and to the use of said composition.

BACKGROUND OF THE INVENTION

Breastfeeding optimally supports the development of the infant and protects against infections. However, not all infants are in the position to receive human milk. It is therefore a continuing aim to provide infant formula, which simulates the functions of human milk. In addition to the desired compositional similarity between infant formula, and human milk, it is also particularly desirable to mimic the protective effects of human milk. Human milk has for example been shown that human milk protects against infections and allergies.

In current infant formulas, the casein to whey ratio resembles that of human milk as closely as possible. It is believed that this ratio results in optimal growth for the infant. However, there are still several downsides attached to the use of bovine, whey dominant protein sources. These whey dominant formulas do not optimally protect against infections. Administration of such formula results in an impaired development of the intestinal flora of the infant compared infants fed with human milk, particularly in the first three to four weeks of life. The flora of infants fed with the whey dominant formula contains more or less the same bacterial genera as the human milk fed infants, however, the quantity of beneficial bacteria is reduced in infants receiving the whey dominant formula compared to infants receiving human milk. Moreover, the flora of infants fed with formulas containing whey dominant bovine protein source contain increased amounts pathological bacteria such as clostridia and enterobacteria. Hence, feeding an infant with whey dominant formula results in the formation of a "suboptimal intestinal flora".

As the very young infants have an immature immune system and an immature intestinal tract, development of the suboptimal intestinal flora may result in infection, diarrhea, allergy and inflammation. Especially infants with the age between 0 and 30 days and fed with bovine whey-dominant protein containing formula suffer from these risk as their faecal flora is most different from those infant fed human milk.

SUMMARY OF THE INVENTION

It is the object of the present invention to provide a nutritional or pharmaceutical composition which reduces the risks attached to feeding whey dominant infant formula.

This object is solved by a composition according to claim 1.

The composition of the present invention is characterized in that the weight ratio of casein to whey is 1:1 to 1:2.4 and that the composition contains:
a) at least 3 grams arginine per 100 grams protein;
b) at least 10 wt. % linoleic acid (LA) based on total fatty acids,
c) at least 1 wt. % alpha linolenic acid (ALA) based on total fatty acids;
d) at least one long chain-polyunsaturated fatty acid (LCPUFA) in an amount exceeding 0.1 wt. % based on total fatty acids, said long chain-polyunsaturated fatty acid (LCPUFA) being selected from the group consisting of docosahexaenoic acid (DHA), arachidonic acid (ARA) and eicosapentaenoic acid (EPA);
e) 5 to 25 wt. % of at least one polyunsaturated fatty acid based on total fatty acids; and
f) 2 to 12 grams indigestible oligosaccharides having a degree of polymerisation of 2 to 100 per 100 gram dry weight of the composition.

The present composition stimulates the maturation of the immune system and the maturation of the intestinal tract. The composition of the invention is particularly suitable for preventing and/or treating inflammatory disorders in infants, such as infection, diarrhea and allergy. The present composition:

stimulates the development of a "optimal intestinal flora" (i.e. a flora similar to the flora resulting by feeding human milk);

stimulates the maturation the gastrointestinal tract, thereby preventing entry of allergens such as pathological bacteria, toxins and food allergens into the systemic circulation;

stimulates the maturation of the immune system, resulting in a better defense in case an allergen, pathogen or toxin crosses the intestinal barrier and/or enters the systemic circulation;

while providing optimal nutrition to the infant.

It is believed that physiological processes underlying the development of a "low risk intestinal flora", the maturation of the gut and the maturation of immune system are highly inter-related and co-dependent. Hence, infant formula should include all those ingredients, in a proper balance, which stimulate the maturation of the gut, the maturation of the immune system and the development of a low risk intestinal flora. With the optimal combination of ingredients, the infant is better protected from allergens. The present composition provides such optimal combination of ingredients. Because the ingredients often act on different mechanisms, the ingredients of the present composition act synergistically, providing the infant with an improved resistance and reducing the incidence of inflammatory disorder, particularly allergy.

The present composition comprises oligosaccharides with a low degree of polymerization. The oligosaccharides stimulate the formation of a low risk intestinal flora, particularly reducing the count of (potentially) pathological intestinal bacteria such as clostridia, enterobacteriae and/or enterococci; and stimulating the colonization by bifidobacteria and lactobacilli. The bifidobacteria and lactobacilli stimulate the maturation of the gut e.g. by stimulating the synthesis of fuco-oligosaccharides by intestinal epithelial cells. Optimal stimulation is achieved by inclusion of a mix of different oligosaccharides, particularly a mix of oligosaccharides including both neutral and acidic oligosaccharides. The oligosaccharides also have a "direct" effect on the immune system through lowering the Th2 response and increasing the Th1 response. It was found that the present composition which includes oligosaccharides can be advantageously used to restore disbalance in the Th1/Th2 responses and for the treatment and prevention of disorders which are associated with Th1/Th2 disbalance, such as autoimmunity and allergy.

However, even when combining oligosaccharides with non-human whey dominant protein, the infants receiving this composition are suffering from increased risks of infections during the first month of life. Hence it is desirable to further improve immune system and/or gut maturity.

It has been surprisingly found that LCPUFA's effectively reduce epithelial paracellular permeability. In contrast to what Usami et al. (Clinical Nutrition 2001, 20(4): 351-359) have reported, it has been found that C18 and C20 polyunsaturated fatty acids, particularly eicosapentaenoic acid (EPA; C20:5 n3) docosahexaenoic acid (DHA; C22:56 n3) and arachidonic acid (AA; C20:4) are capable of effectively reducing intestinal tight junction permeability, thereby stimulating the maturation of the gut. Hence, the present composition advantageously includes LCPUFA's. In addition the essential fatty acids linoleic acid (C18:2 n6) and alpha linolenic acid (C18:3 n3) are indispensable for both maturation of the immune system as well as for maturation of the intestinal tract. In a further particularly preferred embodiment, the present composition also contains gamma-linolenic acid (GLA; C18:3 (n-6)). The present composition therefore contains linoleic acid and alpha linolenic acid.

Optionally, but highly preferably the present composition also comprises nucleotides and/or nucleosides. Nucleotides stimulate the maturation of the intestinal tract, reduce the incidence of diarrhea and stimulates the immune system. Infants fed nucleotide supplemented versus non-supplemented formula have increasing antibody titers following exhibition to antigen and stimulating antigen natural killer cell activity. (Carver et al. Acta Paediatrica, (1999) Vol. 88, No. Sup 430, pp. 83-88).

DETAILED DESCRIPTION

The composition of the present invention comprises a whey dominant non-human protein source, long chain-polyunsaturated fatty acids and oligosaccharides.

As already said above the present invention provides a composition comprising whey and casein in a weight ratio casein to whey of 1:1 to 1:2.4 and at least 3 grams arginine per 100 grams protein.

The range of 1:1 to 1:2.4 for the casein/whey ratio comprises all values lying in this range and therefore for instance the following ratios of casein to whey: 1:1, 1:1.1, 1:1.2, 1:1.3, 1:1.4, 1:1.5, 1:1.6, 1:1.7, 1:1.7, 1:1.9, 1:1.2, 1:1.3, 1:1.4, 1:1.5, 1:1.6, 1:1.7, 1:1.8, 1:1.9, 1:2.0, 1:2.1, 1:2.2, 1:2.3, and 1:2.4. In a preferred embodiment the casein:whey ratio is 1:1.4-1.6, even more preferably about 1:1.5 (40:60)

The arginine is preferably present in an amount of 3 to 8 grams arginine per 100 grams protein component. This range discloses all values and in particular all integer values lying in this range such as 3, 4, 5, 6, 7, and 8 grams. The composition contains preferably 4 to 5 grams arginine per 100 gram protein.

The LCPUFA's present in the composition are selected from the group consisting of DHA, AA and EPA. This means that one or two or three of said long chain-polyunsaturated fatty acids can be present.

The range of 5 to 25 wt.-% given for the polyunsaturated fatty acids discloses all values falling in this range.

The present composition does not include a composition consisting of human milk. The present method does not include a method comprising the administration of a composition consisting of human milk. Hence, preferably the present method includes the administration of a composition comprising a substance of non-human origin, preferably a fiber carbohydrate, fat and/or protein of non-human origin, preferably from plant, animal, bacterial or synthetic origin. Preferably all of the components and constituents out of which the composition of the invention is prepared originate from non-human sources.

Macronutrients

The present composition can be advantageously used as an infant formula. Such infant formula preferably contains a lipid component, a protein component and a carbohydrate component and is preferably administered to the infant in liquid form.

In a preferred embodiment the present invention relates to a composition and in particular to an infant formula which comprises 30 to 60 en % lipid; 5 to 15 en % protein; and 25 to 75 en % carbohydrate. Preferably the composition comprises 5 to 15 en % protein, 30 to 60 en % fat and 25 to 65 en % carbohydrate. More Preferably, the present composition contains 43 to 53 en % lipid; 7 to 11 en % protein; and 43 to 53 en % carbohydrate (en % is short for energy percentage and represents the relative amount each constituent contributes to the total caloric value of the preparation).

The protein component of the present infant formula contains casein and whey in a weight ratio mentioned above. The casein and/or whey are preferably derived from non-human mammalian milk. For providing optimal nutrition to the infant, the composition contains arginine in the specified amount. The term "protein" or protein component in this context is the cumulative of protein, polypeptides, peptides and amino acids. Arginine is indispensable in the present composition. It reduces the incidence of inflammatory conditions of the intestine (Amin et al. Journal of Pediatrics, (2002) Vol. 140, No. 4, pp. 425-431). Furthermore, arginine stimulates the immune system, and is required for maintenance of a healthy immune system (Niever et al., Biomedicine & Pharmacotherapy, (2002) Vol. 56, No. 10, pp. 471-482). Casein and whey contain arginine, but for most milk sources (e.g. bovine whey and casein) the casein and whey provide an insufficient arginine. Preferably at least part of the arginine supplemented to the composition in the form a free amino acid base, e.g. as L-arginine, or in the form of a salt or ester thereof whereby the free amino acid is preferred. The present composition preferably comprises between 75 and 500 mg arginine in the form of free amino acid per 100 gram of the dry infant formula, more preferably with between 150 and 400 mg arginine in the form of free amino acid per 100 gram of the dry infant formula.

The carbohydrate in the present composition is preferably provided largely by lactose, i.e. preferably at least 75 wt. % of total digestible carbohydrate is provided by lactose, preferably at least 90 wt. %.

Low Threonine Protein

Whey dominant infant formulas from non-human protein source typically have a high content of bioavailable threonine compared to human milk. Human milk contains relatively small amounts of bioavailable threonine. Hence, processes for the reduction of the threonine content of whey dominant formulas are provided for in the art (see for example EP1048226, WO0111990 and EP741522). Administering reduced threonine whey dominant infant formula gives in vivo threonine profiles, which are comparable to those of breast fed infants. The present composition preferably is a low-threonine composition, i.e. composition which comprises 2 to 6 grams threonine per 100 gram protein. The low-threonine content can for example be accomplished by using whey products prepared by ultrafiltration or certain acidic whey products.

Essential Fatty Acids Content

The present composition contains at least 10 wt. % linoleic acid (LA) based on total fatty acids, preferably between 11 and 20 wt. %, more preferably between 12 and 15 wt. %. The present composition preferably contains at least 1 wt. % alpha linolenic acid (ALA) based on total fatty acids, preferably between 1.5 and 4 wt. % ALA, even more preferably between 2 and 2.5 wt. %. To reduce intestinal stress, the weight ratio LA/ALA is preferably between 2 and 10, preferably between 5 and 7.5.

The present composition preferably includes between 0.05 and 5 wt % gamma-linolenic acid (GLA) based on total fatty acids, preferably between 0.1 and 1 wt. %.

Long Chain-Polyunsaturated Fatty Acid Content

The present composition comprises at least one long chain-polyunsaturated fatty acid with 20 or 22 carbon atoms (LCPUFA) in an amount exceeding 0.1 wt. % based on total fatty acids, selected from the group consisting of docosahexaenoic acid (DHA), arachidonic acid (AA) and eicosapentaenoic acid (EPA). Preferably the composition contains DHA in an amount exceeding 0.1 wt. % based on total fatty acids; and AA in an amount exceeding 0.1 wt. % based on total fatty acids.

Preferably at least one LCPUFA of this group is included in an amount between 0.15 and 1 wt. % based on total fatty acid content of the composition. Preferably at least two of these LCPUFA's are present in an amount of between 0.15 and 1 wt. % based on total fatty acid content of the composition. Preferably the composition contains AA and DHA, even more preferably AA, DHA and EPA.

The AA content preferably does not exceed 5 wt. %, more preferably does not exceed 1 wt. %, most preferably between 0.1 and 0.6 wt. % of the total fatty acids. In the present composition, EPA and/or DNA are advantageously added to balance the action of AA, e.g. reduce the potential pro-inflammatory action of AA metabolites. Excess metabolites from AA may cause inflammation. Hence, the present composition preferably comprises AA, EPA and/or DHA, wherein the weight ratio AA/DHA preferably is above 0.25, preferably above 0.5, even more preferably above 1. The ratio AA/DHA is preferably below 25, preferably below 10. The weight ratio AA/EPA is preferably between 1 and 100, more preferably between 5 and 20. The weight ratio EPA/DHA is preferably 1 or lower, more preferably below 0.5.

In a preferred embodiment, the content of LCPUFA does not exceed 3 wt. % of the total fatty acids as it is desirable to mimic human milk as closely as possible. For the same reason, the present composition preferably contains less than 1 gram omega-3 LCPUFA per 100 gram fatty acids, more preferably between 0.1 and 0.75 gram per 100 gram fatty acids. The omega-6 LCPUFA content preferably does not exceed 2 gram per 100 gram fatty acids and is preferably between 0.1 and 0.75 gram per 100 gram fatty acids.

The LCPUFAs and the other fatty acids may be provided as free fatty acids, in triglyceride form, in phospholipid form, or as a mixture of one of more of the above. The present composition advantageously comprises at least one of AA and DHA in phospholipid form, as these reduce the incidence of inflammatory disorders of the intestine. The present composition preferably comprises between 0.1 and 5 mg AA from phospholipid per gram total fat and between 0.1 and 5 mg DHA from phospholipid per gram total fat. Preferably the AA and/or DHA are at least partly present in the form of phosphatidylcholine (PC) and/or phosphatidylethanolamine (PE), e.g. AA and/or DHA containing PE and/or PC.

Monounsaturated Fatty Acid

The present nutritional composition preferably also contains omega-9 (n-9) fatty acid (preferably oleic acid, 18:1), to provide sufficient nutrition. Preferably the present composition provides at least 15 wt. % n-9 fatty acid based on the weight of the total fatty acids, more preferably at least 25 wt. %. The content of n-9 fatty acids is preferably below 80 wt. % based on the weight of the total fatty acids. To provide sufficient nutrition, the present composition preferably has a weight ratio saturated fatty acid/polyunsaturated fatty acid between 2 and 5. The weight ratio monounsaturated fatty acid/saturated fatty acid is preferably between 0.5 and 2.

The present composition preferably comprises between 5 and 25 wt. % polyunsaturated fatty acids based on total fatty acids, preferably between 10 and 20 wt. %.

The present composition can be even further improved by inclusion of stearidonic acid (C18:4n3). The composition preferably contains between 0.05 and 2 wt. % stearidonic acid based total fatty acids, even more preferably between 0.1 and 1 wt. %.

Oligosaccharides

The present composition comprises 2 to 12 grams indigestible oligosaccharides with a degree of polymerisation (DP) of 2 and 100 per 100 gram dry weight of the composition, preferably between 3 and 8 grams, more preferably between 5 and 7.5 grams. After reconstitution of the powder in liquid and administration of the liquid formula to the infant, these amounts of indigestible oligosaccharides provide the desired effects without causing intestinal discomfort. Suitable indigestible oligosaccharides are not or only partially digested in the intestine by the action of acids or digestive enzymes present in the human upper digestive tract (small intestine and stomach), but are fermentable by the human intestinal flora. The oligosaccharides are preferably water-soluble (exceeding a solubility of 1 gram oligosaccharide per liter water). The average DP of the present oligosaccharide is preferably below 40, even more preferably below 20. Optimally, the present composition comprises between 2 and 12 grams oligosaccharides with a DP of 2 to 60, more preferably with a DP of 2 to 10 (i.e. the sum of the weights of those oligosaccharides with a DP of 2, 3, 4, 5, 6, 7, 8, 9 and 10).

According to a further embodiment at least one of the oligosaccharides of the present composition is selected from the group consisting of inulin, fructooligosaccharides, indigestible dextrins, galactooligosaccharides (including transgalactooligosaccharides), xylooligosaccharides, arabinooligosaccharides, glucooligosaccharides, mannooligosaccharides, lacto-N-neotetraose, fucooligosaccharides (containing at least one fucose saccharide unit), acidic oligosaccharides (see below, e.g. uronic acid oligosaccharides such as pectin hydrolysate) and mixtures thereof.

Preferably the present composition comprises at least one selected from the group consisting of inulins and fructooligosaccharides and at least one selected from the group consisting of galactooligosaccharides (including transgalactooligosaccharides) and pectin hydrolysate. In a particularly preferred embodiment, the present composition comprises 2 to 12 grams oligosaccharides with a DP of 2 to 10 and β-linked galactose and glucose saccharides, more preferably transgalactooligosaccharides (i.e. [gal]$_n$-glu, wherein n is 2 to 10). In a particularly preferred embodiment, the present composition comprises transgalactooligosaccharides (i.e. [gal]$_n$-glu, wherein n is 2 to 10), pectin hydrolysate and at least one selected from the group consisting of fructooligosaccharides and inulin. The present oligosaccharide can also be an oligosaccharide derived from animal milk, a mixture of oligosaccharides derived from animal milk or a fucosylated oligosaccharide (oligosaccharide containing at least one fucose saccharide unit).

For further improvement of gut maturation over the whole area of the colon, preferably at least 10 wt. % of the oligosaccharides in the present composition has a DP of 2 to 5 (i.e. 2, 3, 4 and/or 5) and at least 5 wt. % has a DP of 10 to 100. Preferably at least 50 wt. %, more preferably at least 75 wt. % of the oligosaccharides have a DP of 2 to 10 (i.e. 2, 3, 4, 5, 6, 7, 8, 9 and/or 10), because these are believed to work throughout the ileum and proximal and middle parts of the colon and because the weight percentage of oligosaccharides that needs to be incorporated in the composition to achieve the desired effect is reduced.

Preferably the Weight Ratios:
(oligosaccharides with DP 2 to 5): (oligosaccharides with DP 6 to 9); and (oligosaccharides with DP 10 to 100): (oligosaccharides with DP 6 to 9) are both above 1.

Preferably both weight ratios are above 2, even more preferably above 5.

The present composition preferably comprises 0.5 to 10 gram galactooligosaccharide with DP between 2 and 10 per 100 gram dry weight of the composition, more preferably between 1 and 5 gram. The preferred galactooligosaccharides is transgalactooligosaccharide, as this best mimics human milk oligosaccharides. The present invention preferably comprises 0.5 to 10 gram fructopolysaccharide with DP between 10 and 60 per 100 gram dry weight of the composition, more preferably between 1 and 5 gram. The term "fructopolysaccharide" refers to a polysaccharide carbohydrate comprising a chain of at least 10 β-linked fructose units.

Acidic Oligosaccharides

To further improve barrier integrity, the present composition preferably includes acidic oligosaccharides with a DP between 2 and 100, preferably 2 to 60. The term acid or acidic oligosaccharide refers to oligosaccharides comprising at least one acidic group selected from the group consisting of N-acetylneuraminic acid, N-glycoloylneuraminic acid, free or esterified carboxylic acid, sulfuric acid group and phosphoric acid group. The acidic oligosaccharide preferably comprises uronic acid units (i.e. uronic acid polymer), more preferably galacturonic acid units. The present composition preferably contains between 0.1 and 10 grams acid oligosaccharides per 100 gram dry weight of the present composition, more preferably between 1 and 6 grams per 100 gram dry weight.

Structure I: Polymeric Acid Oligosaccharide

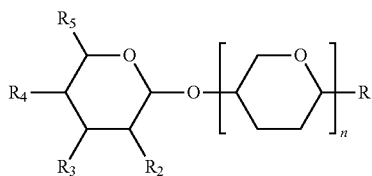

wherein:
R is preferably selected from the group consisting of hydrogen, hydroxy or acid group, preferably hydroxy; and
at least one selected from the group consisting of R2, R3, R4 and R5 represents N-acetylneuraminic acid, N-glycoloylneuraminic acid, free or esterified carboxylic acid, sulfuric acid group and phosphoric acid group, and the remaining of R2, R3, R4 and R5 representing hydroxy and/or hydrogen. Preferably one selected from the group consisting of R2, R3, R4 and R5 represents N-acetylneuraminic acid, N-glycoloylneuraminic acid, free or esterified carboxylic acid, sulfuric acid group or phosphoric acid group, and the remaining represent hydroxy and/or hydrogen. Even more preferably one selected from the group consisting of R2, R3, R4 and R5 represents free or esterified carboxylic acid and the remaining of R2, R3, R4 and R5 representing hydroxy and/or hydrogen; and
n is an integer and refers to a number of hexose units (see also Degree of Polymerisation, below), which may be any hexose unit. Suitably n is an integer between 1-5000. Preferably the hexose unit(s) is a uronic acid unit.

Most preferably R1, R2 and R3 represent hydroxyl, R4 represent hydrogen, R5 represents carboxylic acid, n is any number between 1 and 250, preferably between 1 and 10 and the hexose unit is galacturonic acid.

The detection, measurement and analyses of the preferred acid oligosaccharides as used in the present method are given in applicants earlier patent application relating to acid oligosaccharides, i.e. WO 0/160378.

Preferably, the acid oligosaccharide has one, preferably two, terminal uronic acid units, which may be free or esterified. Preferably the terminal uronic acid unit is selected from the group consisting of galacturonic acid, glucuronic acid, guluronic acid, iduronic acid, mannuronic acid, riburonic acid and altruronic acid. These units may be free or esterified. In an even more preferred embodiment, the terminal hexose unit has a double bond, which is preferably situated between the C4 and C5 position of the terminal hexose unit. Preferably one of the terminal hexose units comprises the double bond. The terminal hexose (e.g. uronic acid) preferably has a structure according to the following structure II:

Structure II: Preferred terminal hexose acid group

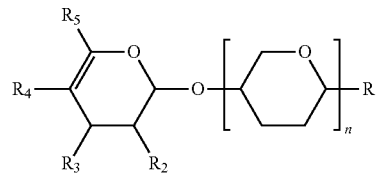

wherein;
R is preferably selected from the group consisting of hydrogen, hydroxy or acid group, preferably hydroxy (see above); and
at least one selected from the group consisting of R2, R3, R4 and R5 represents N-acetylneuraminic acid, N-glycoloylneuraminic acid, free or esterified carboxylic acid, sulfuric acid group and phosphoric acid group, and the remaining of R2, R3, R4 and R5 representing hydroxy and/or hydrogen. Preferably one selected from the group consisting of R2, R3, R4 and R5 represents N-acetylneuraminic acid, N-glycoloylneuraminic acid, free or esterified carboxylic acid, sulfuric acid group and phosphoric acid group, and the remaining of R2, R3, R4 and R5 represent hydroxy and/or hydrogen. Even more preferably one selected from the group consisting of R2, R3, R4 and R5 represents free or esterified carboxylic acid and the remaining of R2, R3, R4 and R5 represent hydroxy and/or hydrogen; and n is an integer and refers to a number of hexose units (see also Degree of Polymerisation, below), which may be any hexose unit. Suitably n is an integer between 1-5000 representing the number of hexose units said hexose units preferably being uronic acid, even more preferably being galacturonic acid units. The carboxylic acid groups on these units may be free or (partly) esterified, and are preferably at least partly methylated.

Most preferably, R2 and R3 represent hydroxy, R4 represent hydrogen and R5 represents free or esterified carboxylic acid.

The acid oligosaccharides used in the invention are preferably prepared from pectin, pectate, alginate, chondroitine, hyaluronic acids, heparine, heparane, bacterial carbohydrates, sialoglycans, fucoidan, fucooligosaccharides or carrageenan, more preferably from pectin and/or alginate. Preferably pectin hydrolysate is used.

Nucleotides

The present composition preferably also comprises between 5 and 100 mg nucleosides and/or between 5 and 100 mg nucleotides per 100 gram dry weight of the composition, more preferably between 5 and 50 mg. The nucleotides and/or nucleosides further stimulate the immune system, acting synergistically with the other ingredients of the present composition.

Zinc

Zinc is an essential micronutrient for growth and development of the immune function. Zinc deficiency impairs overall immune function and resistance to infection. Hence the present composition advantageously comprises zinc, preferably in an amount 2 to 100 mg zinc per 100 gram dry weight of the present composition, even more preferably at least 4-25 mg zinc per 100 g dry weight of the present composition. The weight of zinc is calculated as elementary zinc.

Liquid

The present composition is preferably in powder or liquid form or an tablet form, wherein said tablet has a weight between 5 and 25 grams. Preferably, the present composition is provided in powered form as this increases shelf life. The present composition is preferably administered orally in liquid form. Prior to the administration of the present composition, it is preferably admixed with a liquid, preferably water. As the liquid composition is preferably administered while having a temperature of 35-40° C. (preferably about 37° C.), the liquid formula is preferably prepared by:

Process a: mixing water with a temperature below of 30° C. and the composition according to any one of claims 1-10, in a weight ratio water: composition of 1-10:1; and heating the mixture obtained in step a) to a temperature between 35 and 50° C.; or Process b: mixing water with a temperature below of 60° C. and the composition according to any one of claims 1-10, in a weight ratio water: composition of 1-10:1; and cooling the mixture obtained in step a) to a temperature between 35 and 40° C. Process a) is more suitable for preparation of liquid formula from powder, while process b) is more suitable for preparing a liquid formula from the tablet.

Stool irregularities (e.g. hard stools, insufficient stool volume, diarrhea) is a major problem in many babies and ill subjects that receive liquid foods.

It was found that stool problems may be reduced by administering the present composition in liquid form, having an osmolality between 50 and 500 mOsm/kg, more preferably between 100 and 400 mOsm/kg, most preferably between 220 and 300 mOsm/kg.

In view of the above diarrhea problem, it is also important that the liquid food does not have an excessive caloric density as this causes significant intestinal stress. However, the formula needs to provide sufficient calories to feed the infant. Hence, the liquid food preferably has a caloric density between 0.5 and 0.9 kcal/ml, preferably between 0.6 and 0.8 kcal/ml.

Application

The present composition is advantageously administered to infants with the age between 0 and 2 years. The present composition can also be advantageously used in a method for providing the nutritional requirements of a premature infant (an infant born before 37 weeks gestation). In a preferred embodiment, the present invention provides a method for feeding infants with an age between 0 and 30 day.

The present composition can be advantageously used to treat or prevent diseases wherein a comprised immune system and/or intestinal barrier immaturity is underlying the development of the course of the disease. The present composition can thus be advantageously used to treat or prevent diarrhea or allergy, particularly in infants with an age between 0 and 2. The present composition is particularly suitable for the treatment and/or prevention of allergic rhinitis, allergic conjunctivitis, allergic dermatitis, atopic dermatitis and/or food allergy.

The present composition is preferably provided as a packaged powder or packaged ready-to-feed formula. To prevent spoilage of the product, packaging size of ready-to-feed formula preferably does not exceed one serving, e.g. preferably does not exceed 500 ml; and packaging size of the present composition in powder form preferably does not exceed 250 servings. Suitable packaging sizes for the powder are 2000 grams or less, preferably per 1000 grams or less.

The packaged products provided with labels that explicitly or implicitly direct the consumer towards the use of said product in accordance with one or more of the above or below purposes, are encompassed by the present invention. Such labels may for example including wording like, "stimulates maturation of the intestine and/or immune system", "reduces allergic reaction", "less stress", "improved resistance" or "reduced sensitivity" or similar wording.

It is therefore a subject matter of the present invention to use the composition as described herein for the manufacture of a formula food or a medicament to be administered to a mammal for the treatment and/or prevention of an inflammatory disease, of diarrhea, of eczema and/or of atopic dermatitis.

It is furthermore a subject matter of the present invention to use the composition as described herein for the manufacture of a medicament for use in a method for the treatment and/or prevention of an inflammatory disease, of diarrhea, of eczema and/or of atopic dermatitis said method comprising administering said composition enterally or per os to a mammal and in particular to a human infant. In a preferred embodiment, the present method provides for a method for the treatment and/or prevention of infections, said method comprising administering the present composition.

The invention is described furthermore by the following examples:

EXAMPLE 1

Infant nutrition

A liquid infant nutrition, prepared by admixing 13.9 g powder with water to yield 100 ml final product, said liquid product comprising per 100 ml:

Energy: 66 kcal
Protein: 8 en %
  1.3 g (containing 0.6 g casein; 0.8 g whey; 0.072 g L-arginine)
Digestible Carbohydrates: 44 en %
  7.4 g (containing 7.3 g lactose)

Fat: 48 en %
3.5 g (containing 0.41 g linoleic acid; 0.08 g α-linolenic acid; 0.012 g arachidonic acid; 0.002 g eicosapentanoic acid; 0.006 g docosahexaenoic acid; 1.4 g oleic acid;)
Fibre: 0.8 g (containing 0.05 g fructopolysaccharide (Raftiline HP™, Orafti, Tienen, Belgium); 0.55 g transgalactooligosaccharides (Vivinal-GOS™ (Borculo Domo Ingredients, Netherlands); 0.20 g pectin hydrolysate prepared as described in EP1373543, example 1.
Nucleotides: 0.89 mg Cytidine-5-monophosphate;
  0.55 mg Uridine-5-monophosphate;
  0.82 mg Adenosine-5-monophosphate;
  0.20 mg Guanosine-5-monophosphate;
  0.34 mg Inosine-5-monophosphate.
Osmolarity: 300 mOsmol/l The composition further contains choline (6 mg/100 ml) and taurine (6.3 mg/100 ml); minerals and trace elements (including 2 mg zinc/100 ml) and vitamins in amounts in compliance with the international guidelines for infant milk formula.

EXAMPLE 2

Packaged infant milk formula according to example 1, wherein the packaging is provided with a label indicating that the formula can be suitably used to prevent or treat allergy.

EXAMPLE 3

Experimental Setup

The effect of diets comprising acid oligosaccharides, optionally combined with neutral oligosaccharides were tested on the delayed-type hypersensitivity (DTH) response, which is a parameter for Th1 immunological response and is determined by measuring the increase in ear swelling after local antigen challenge.

Acid oligosaccharides (AcOl) used, with an average DP between 2 and 10, were obtained by the method described in WO 02/42484 (see example 1). Diets containing 1 wt. %, 2.5 wt. %, 5 wt. % and 10% wt. % AcOl based on total weight of the diet were tested. Neutral oligosaccharide mixture (GF) containing galactooligosaccharides (GOS) (Vivinal-GOS™ (Borculo Domo Ingredients, Netherlands) and fructooligosaccharides (FOS) (Raftiline HP™, Orafti, Tienen, Belgium) were used in a weight ratio GOS:FOS of 9:1. Diets containing 1, 2.5 and 5 wt. % GF based on total weight of the diet were tested. The effects of a combination of acid and neutral oligosaccharides (GF and AcOl) was tested in a diet containing 1 wt. % GF and 1 wt. % AcOl based on total weight of the diet.

All data is presented as percentages relative to control values, i.e. the relative values of the oligosaccharide supplemented group compared to the group receiving the control diet (without oligosaccharides).

Animals and Diets

Female, 6 weeks old C57Bl/6 mice (Harlan Nederland B V, Horst, the Netherlands) were group-housed under a regular 12 hours light/dark regime. Group size was 10 animals per group and 3 animals in the negative control groups. The animals were given semi-synthetic diets (Research Diet Services, Wijk bij Duurstede, the Netherlands). Control diets were made to the AIN93G specifications (Reeves et al. (1993) Development and Testing of the AIN93 purified diets for rodents: results on growth kidney calcification and bone mineralisation in rats and mice. J Nutrition 123(11): 1923-31), oligosaccharide supplemented diets were based on these specifications. Carbohydrate content of the supplemented diets were kept constant by the exchange of total carbohydrates for the oligosaccharides on a weight basis. The separate carbohydrate components were substituted respective to their normal ratio in the diet. The carbohydrates in the normal diet consist of cornstarch (40% of total weight), dextrinized cornstarch (13.2%), sucrose (10%) and cellulose (5%).

Vaccination Protocol

Vaccinations were started after a period of two to four weeks of adaptation to the new housing and diets. At day 0, a blood sample was collected prior to vaccination. At day 1, the first vaccination was administered subcutaneously. After three weeks, a blood sample was collected (day 21) and a booster vaccination was given (day 22). Nine days after booster injection (day 31), basal ear thickness was measured with a Digimatic outside micrometer (Mitutoyo, Veenendaal, the Netherlands) and a delayed-type hypersensitivity (DTH) response was induced by injecting antigen solution i.c. (intracutaneous) in the mouse ear pinnae. 24 h therafter (day 32), the DTH response was measured, a bloodsample was taken and the mice were sacrificed. Spleens were isolated and prepared for ex-vivo restimulations.

The vaccinations consisted of a 100 μl i.c. (intracutaneous) injection of a 1:1 mix of antigen solution and Stimune adjuvant (Specol, Cedidiagriostics B V, Lelystad, the Netherlands). The antigen solution was a 1:100 dilution of Influvac 2002/2003 (Solvay Pharmaceuticals, Weesp, the Netherlands) in PBS. Influvac is a trivalent protein vaccine, containing 3×30 μg/ml haemagglutinin of three different influenza strains.

For the DTH responses, mice were i.c. injected with 25 μl dialysed Influvac in both ears as a DTH challenge.

Cell Cultures

Splenocytes were isolated from the spleens using fine-mesh cell strainers (Becton Dickinson, Erembodegem, Belgium). Red blood cells were lysed by 5 minutes incubation on ice. After washing with culture medium without phenol red, cells were counted (Coulter Counter, Beckman Coulter, the Netherlands) and kept on ice. Cultures were set up using 0.1 μg/ml dialysed Influvac as a stimulus. Cells were seeded in 96-well culture plates at $1*10^6$ cells per well. The culture medium consisted of RPMI-1640 with HEPES buffer and 2 mM L-Glutamine (Invitrogen, Merelbeke, Belgium) with 10% fetal calf seium (FCS). Cultures were incubated for 5 days at 37° C. at 5% $CO_2$. Thereafter supernatants were harvested and frozen at −80° C. until analysis. Cell proliferation was measured in parallel cultures by $^3$H-thymidine incorporation, which was added to the cultures for the last 18 hours at 0.4 μCu/well. After 5 days, the cells were harvested using a Filtermate harvester (Perkin Elmer, Zaventem, Belgium) and counted on a Micro-Beta counter (Perkin Elmer, Zaventem, Belgium). Radioactive decay was measured for 1 minute per well and the counts per minute (cpm) were recorded as a measure for proliferation speed.

Cytokines were analysed in supernatants of Influvac stimulated cultures. IL-2, IL-5, IL-10 and IFN-gamma were measured using the Bio-Plex system with a custom mixed beadset for the cytokines mentioned (Bio-Rad, Veenendaal, the Netherlands). Cytokines were measured according to the manufacturer's specifications. IL-4 was measured by ELISA using the Pharmingen OptElA mouse IL-4 kit (Becton Dickinson, Erembodegem, Belgium), according the manufacturer's specifications.

Results

DTH Response Acid Oligosaccharides

The diets containing dosages of 1 wt. %, 2.5 wt. % and 5 wt. % AcOl induced a statistically significant increase in the DTH response, showing a dose-dependent increase (see Table 1). The observed effect is indicative for the advantageous use of acid oligosaccharides in the present method.

TABLE 1

| Wt % acid oligosaccharides in diet | DTH response (%) |
|---|---|
| 0 (control) | 100 |
| 1 | 122 |
| 2.5 | 136* |
| 5 | 140* |

*indicates significantly different (P < 0.05) from control

DTH Response Acid and Neutral Oligosaccharides

The combination of 1 wt. % GF, 2.5 wt. % GF and the mixture of 1 wt. % GF and 1 wt. % AcOl induce a statistically significant increase in the DTH (see Table 2). The observed effect is indicative for the advantageous use of a indigestible oligosaccharides, particularly the combination of acid and neutral oligosaccharides in the present method.

TABLE 2

| Wt % acid oligosaccharides in diet | DTH response (%) |
|---|---|
| 0 (control) | 100 |
| 1 wt % GF | 132* |
| 1 wt. % AcOl | 122 |
| 2.5 wt % GF | 129* |
| 2.5 wt. % AcOl | 136* |
| 1 wt. % GF and 1 wt. % AcOl | 159* |

*indicates significantly different (P < 0.05) from control

Influvac Specific Proliferation of Acid Oligosaccharides

Administration of diets containing 2.5 wt % and 5 wt. % acid oligosaccharides (AcOl) induced a significant lowering effect on the influvac specific proliferation ex vivo (see Table 3). The observed effect is indicative for the advantageous use of acid oligosaccharides in the present method.

Influvac Specific Proliferation of a Combination of Acid and Neutral Oligosaccharides Administration of a combination of 1 wt. % GF and 1 wt. % AcOl induced significant lowering effects on the antigen specific proliferation (see Table 3). As the effect is significantly improved over the DTH responses from diets containing the acid or neutral oligosaccharides alone, these results are indicative for the synergistic effect provided by the administration of acid and neutral oligosaccharides. The observed effect is indicative for the advantageous use of a combination of acid and neutral oligosaccharides in the present method. Reduced proliferation is indicative for the reduction of Th2 response, and the Th1/Th2 balancing effect of the present method.

TABLE 3

| Wt. % oligosaccharides in diet | Influvac specific proliferation (%) |
|---|---|
| 0 (control) | 100 |
| 1 wt % GF | 100 |
| 1 wt. % AcOl | 92 |
| 2.5 wt. % AcOl | 61* |
| 5 wt. % AcOl | 54* |
| 1 wt. % GF and 1 wt. % AcOl | 50* |

*indicates significantly different (P < 0.05) from control

Th1/Th2 Balance: Cytokine Profiles after Administration of Acid Oliposaccharides Cytokine profiles were measured in the culture supernatants of the influvac specific splenocytes. Data are presented as percentage relative to values of the vaccinated control group (i.e. receiving no oligosaccharides). Compared to controls, diets containing 2.5 wt. % and 5 wt. % AcOl resulted in a decrease in the Th2-related cytokines IL-4, IL-5 and IL-10, while the Th1-related cytokines IL-2 was increased and IFN-γ was not significantly lowered (see Table 4). These results are indicative for the Th1/Th2 balancing effect of acid oligosaccharides and indicative for the advantageous use of acid oligosaccharides in the present method, e.g. for the treatment and/or prevention of diseases with relatively low Th1 immunity.

Th1/Th2 Balance: Cytokine Profiles after Administration of Acid and Neutral Oligosaccharides Compared to controls, administration of a combination of 1 wt. % GT and 1 wt. % acOl resulted in a decrease in the Th2-related cytokines IL-4, IL5 and IL-10, while the TM-related cytokines IL-2 and IFN-γ were not lowered (see Table 4, wherein data are presented as percentage relative to values of the vaccinated control group (i.e. receiving no oligosaccharides)). These results are indicative for the Th1/Th2 balancing effect of a combination of acid- and neutraf oligosaccharides and indicative for the advantageous use of acid oligosaccharides in the present method, e.g. for the treatment and/or prevention of diseases with relatively low Th1 immunity. Particularly the IL-4/IFN ratio reflects the Th2/Th1 balance. In other words, a lower ratio is indicative for stimulation of Th1 and/or inhibition of Th2, and in any case indicative for the Th1-Th2 balancing effect of the present oligosaccharides.

TABLE 4

| | cytokine | | | | | |
|---|---|---|---|---|---|---|
| Wt. % oligosaccharides | IFN-γ (%) | IL2 (%) | IL10 (%) | IL4 (%) | IL5 (%) | IL4/IFN-γ ratio |
| 0 (control) | 100 | 100 | 100 | 100 | 100 | 100 |
| 1 wt. % AcOl | 100 | 196* | 70 | 83 | 72 | 85 |
| 2.5 wt. % AcOl | 75 | 116 | 58* | 55 | 66 | 75 |
| 5 wt. % AcOl | 69 | 161 | 44* | 33* | 56* | 51* |
| 1 wt. % GF and 1 wt. % AcOl | 93 | 123 | 45* | 44* | 55* | 45* |

*indicates significantly different (P < 0.05) from control

The invention claimed is:

1. A method for the treatment of an inflammatory disease, diarrhea, eczema and/or atopic dermatitis, comprising administering to a mammal in need thereof an infant formula composition comprising fat, carbohydrate, protein,
    (a) whey and casein in a weight ratio of casein to whey from 1:1 to 1:2.4, and
    (b) 2 to 12 grams of a combination of neutral and acidic indigestible oligosaccharides having a degree of polymerization of 2 to 100 per 100 gram dry weight of the composition,
    wherein 1 to 10 grams of the combination comprises acidic oligosaccharides, and wherein the neutral indigestible oligosaccharides comprise galactooligosaccharides (GOS) and fructooligosaccharides (FOS) in a GOS:FOS weight ratio of 9:1.

2. The method according to claim 1, wherein the inflammatory disease is an allergy.

3. The method according to claim 1, wherein the composition is administered enterally or per os.

4. The method according to claim 1, wherein the composition comprises docosahexaenoic acid, arachidonic acid and/or eicosapentaenoic acid.

5. The method according to claim 1, wherein the composition further comprises 2 to 100 mg zinc per 100 gram dry weight of the composition.

6. The method according to claim 1, wherein the composition comprises 5 to 15 wt. % protein; 30 to 60 wt. % fat; and 25 to 75 wt. % carbohydrate.

7. The method according to claim 1, wherein the composition further comprises between 5 and 100 mg nucleotides and/or between 5 and 100 mg nucleosides per 100 gram dry weight of the composition.

8. The method according to claim 1, wherein the composition further comprises 2 to 6 grams threonine per 100 gram total protein.

9. The method according to claim 1, wherein the composition comprises docosahexaenoic acid in an amount exceeding 0.1 wt. % based on total fatty acids and arachidonic acid in an amount exceeding 0.1 wt. % based on total fatty acids and that the weight ratio arachidonic acid/docosahexaenoic acid is between 0.25 and 25.

10. The method according to claim 1, wherein the infant formula comprises:
   a) at least 3 grams arginine per 100 grams total protein;
   b) at least 10 wt. % linoleic acid based on total fatty acids;
   c) at least 1 wt. % alpha linolenic acid based on total fatty acids;
   d) at least one long chain-polyunsaturated fatty acid in an amount exceeding 0.1 wt. % based on total fatty acids, said long chain polyunsaturated fatty acid being selected from the group consisting of docosahexaenoic acid, arachidonic acid and eicosapentaenoic acid; and
   e) 5 to 25 wt. % of at least one polyunsaturated fatty acid based on total fatty acids.

11. The method according to claim 1, wherein the treatment is of an inflammatory disease.

12. The method according to claim 1, wherein the treatment is of diarrhea.

13. The method according to claim 1, wherein the treatment is of eczema and/or atopic dermatitis.

14. The method according to claim 1, comprising 2 to 8 grams of a combination of neutral and acidic indigestible oligosaccharides having a degree of polymerization of 2 to 100 per 100 gram dry weight of the composition, wherein 1 to 6 grams of the combination comprises acidic oligosaccharides.

* * * * *